United States Patent [19]
Sato et al.

[11] Patent Number: 5,977,130
[45] Date of Patent: Nov. 2, 1999

[54] INTIMAL HYPERTROPHY INHIBITORS

[75] Inventors: Atsushi Sato, Hanno; Tetsuji Asao, Tokorozawa; Yuichi Hagiwara, Iruma; Makoto Kitade, Hanno; Yasundo Yamazaki, Iruma, all of Japan

[73] Assignee: Taiho Pharmeutical Co., Ltd., Tokyo, Japan

[21] Appl. No.: 08/913,237

[22] PCT Filed: Jan. 16, 1997

[86] PCT No.: PCT/JP97/00065

§ 371 Date: Sep. 10, 1997

§ 102(e) Date: Sep. 10, 1997

[87] PCT Pub. No.: WO97/25986

PCT Pub. Date: Jul. 24, 1997

[30] Foreign Application Priority Data

Jan. 17, 1996 [JP] Japan .................................. 8-005693

[51] Int. Cl.⁶ .......................... A61K 31/40; A61K 31/44
[52] U.S. Cl. .......................... 514/300; 514/339; 514/418; 546/113; 546/256; 546/277.7; 548/486
[58] Field of Search .................. 514/300, 339, 514/418

[56] References Cited

U.S. PATENT DOCUMENTS

| | | | |
|---|---|---|---|
| 3,413,299 | 11/1968 | Anthony | 546/15 |
| 3,428,649 | 2/1969 | Plostnicks | 548/486 |
| 4,002,749 | 1/1977 | Rovnyak | 514/227.2 |
| 5,206,261 | 4/1993 | Kawaguchi et al. | 514/418 |

FOREIGN PATENT DOCUMENTS

| | | |
|---|---|---|
| 363671 | 9/1988 | European Pat. Off. . |
| 580502A1 | 7/1992 | European Pat. Off. . |
| 2152282 | 10/1970 | Germany . |
| 65452 | 12/1992 | Hungary . |
| 62029570 | 7/1985 | Japan . |
| 2-121922 | 5/1990 | Japan . |
| 9207830 | 5/1992 | WIPO . |
| 9501349 | 1/1995 | WIPO . |
| 9514667 | 6/1995 | WIPO . |
| 96/40116 | 12/1996 | WIPO . |

OTHER PUBLICATIONS

Epoxides by the action of diaryldiazomethanes on ketones, Alexander Schoenberg and Klaus Junghans, Ber. 96 (12), 3328–37 (1963), vol. 60;4086a.

Synthesis and cardiotonic activity of 2–indolinones, Aldo Andreani, et al., Eur. J. Med. Chem. (1990) 25, 187–190.

Synthesis and cardiotonic activity of pyridylmethylene–2–indolinones, A. Andreani, et al., Eur. J. Med. Chem (1992) 27, 167–170.

Primary Examiner—Richard L. Raymond
Attorney, Agent, or Firm—Sughrue, Mion, Zinn, Macpeak & Seas, PLLC

[57] ABSTRACT

The present invention is directed to an intimal hypertrophy inhibitor containing as the active ingredient an oxyindole derivative represented by the following formula (I) or a salt thereof:

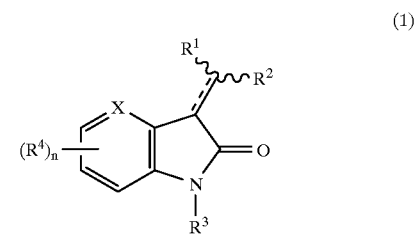

(1)

(wherein $R^1$ represents a hydrogen atom; a phenyl group which may be substituted by a lower alkyl group, a lower alkoxy group, a lower alkylaminoalkoxy group, a hydroxy group, an amino group, a lower alkylamino group, or a halogen atom; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group; $R^2$ represents a phenyl group which may be substituted; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group; $R^3$ represents a hydrogen atom; a lower alkyl, benzyl, or a benzenesulfonyl group which may be substituted; or an acyl group; $R^4$ represents a hydrogen atom; a lower alkoxy group, a halogen atom, an amino group, a lower alkylamino group, a carboxyl group, a lower alkoxycarbonyl group; a phenylcarbomoyl group which may be substituted; or a trifluoromethyl group; X represents CH or N; n represents a number between 0 and 4 inclusive that indicates the number of substituents; and the broken/solid double line denotes a single bond or a double bond). The intimal hypertrophy inhibitor of the present invention exhibits excellent inhibitory action against intimal hypertrophy, and thus is useful as a preventive/therapeutic/ameliorating agent for proliferative vascular diseases such as restenosis after PTCA, arteriosclerosis, peripheral embolism, and angiitis.

6 Claims, 2 Drawing Sheets

INTIMAL HYPERTROPHY INHIBITORS

This application is a 371 of PCT/JP 97/00065, filed Jan. 16, 1997.

TECHNICAL FIELD

The present invention relates to intimal hypertrophy inhibitors containing an oxindole derivative as the active ingredient.

BACKGROUND ART

Coronary arteriosclerosis is known to precede and be the major cause of the onset of various pathological conditions such as angina pectoris and myocardial infarction. Luminal narrowing caused by arteriosclerosis and loss of vascular elasticity bring about deficiency of nutrition and oxygen in cardiac muscular tissue, to thereby induce the aforementioned pathological conditions. Narrowing of vascular lumina is considered to be primarily caused by accumulation of foamy macrophages and cholesterol on the inner wall, and in addition, by cell-fibrous intimal hypertrophy caused by migration of smooth muscle cells of the media into the intima, and proliferation of the cells in the intima. In the treatment of angina pectoris and myocardial infarction, antithrombotic agents, vasodilator agents, etc. have been used for the principal purpose of ameliorating the symptoms. However, these agents have failed to serve as a radical remedy for the narrowing and loss of elasticity of vascular lumina caused by arteriosclerosis. Therefore, pharmaceuticals that are capable of preventing or treating intimal hypertrophy which causes angiostenosis are earnestly desired.

In recent years, angiostenosis has been surgically treated by percutaneous transluminal coronary angioplasty (hereinafter referred to as PTCA). PTCA is a therapy in which a balloon catheter is inserted by remote operation into the narrow segment through, for example, the femoral artery, without performance of thoracotomy, and the balloon is inflated in situ, to thereby physically achieve vasodilation. Due to advancement in manipulation technique of PTCA, more than 90% of PTCA cases show amelioration of symptoms immediately after PTCA. In addition, PTCA rarely involves death or signs of adverse side effects such as induction of myocardial infarction. Accordingly, PTCA is accepted as an excellent therapy. However, about 30–40% of the cases that undergo PTCA revert to restenosis at the same site, and if restenosis occurs, PTCA must be performed again, or alternatively, an aorta bypass-forming operation must be performed. This constitutes the most significant problem in the clinical field. Autopsy of cases in which death was caused by reblockage after PTCA revealed that intimal hypertrophy had occurred at the site at which the vascular cavity had been dilated, thus reblocking the site [see, for example, British Heart Journal, 58, 635–643 (1987), Human Pathology, 477–485 (1989)].

Therefore, it is considered that inhibition of intimal hypertrophy would be effective for the prevention of restenosis after PTCA and further for the treatment of arteriosclerosis.

The pharmaceuticals that were expected to open the way up to the remedy of the aforementioned diseases have been studied in both preclinical and clinical stages [American Heart Journal, 122, 171–187 (1991)]. The candidate pharmaceuticals were anticoagulants such as heparin; platelet aggregation inhibitors such as aspirin, dipyridamole, ticlopidine, prostacycline, and their derivatives; thromboxane A2 inhibitors such as trapidil; cell proliferation inhibitors such as ketanserin; calcium antagonists such as diltiazem and nifedipine; lipid decreasing agents such as fish oil, eicosapentaenoic acid and lovastatin; and anti-inflammatory agents such as steroids. However, after actual investigation in clinical situations, none of these drugs were found to have clear utility.

Tranilast is an intimal hypertrophy inhibitor considered to be developed to the most advanced level (Japanese Patent Application Laid-Open (kokai) No. 6-135829). However, due to its weak activity, this drug is not a satisfactory intimal hypertrophy inhibitor.

Thus, presently there are no effective drugs against intimal hypertrophy, and therefore, clinically useful pharmaceuticals are strongly called for.

The active ingredients of the present invention, oxindole derivatives, partially comprise known compounds. The known compounds include synthesis intermediates disclosed in Japanese Patent Publication (kokoku) No. 43-3195, Hungarian Patent Application Laid-Open No. 65452, U.S. Pat. No. 4,002,749, Chem. Ber. 91, 2095 and 91, 1898 (1958), and U.S. Pat. No. 3,413,299; UV absorbers disclosed in U.S. Pat. No. 3,428,649; antidepressant agents or tranquilizers disclosed in Japanese Patent Application Laid-Open (kokai) No. 47-8628; antinootropic agents disclosed in WO 91/01306; drugs for the treatment of central nervous diseases or stomach ulcers disclosed in WO 92/07830; and drugs for the treatment of asthma, rheumatic arthritis, and allergic rhinitis disclosed in WO 95/14667. In addition, myocardial infarction augmenting effect of these compounds is disclosed in European Journal of Medicinal Chemistry, 25(2), 187 (1990), ibid. 27(2), 167 (1992), and ibid. 28, 653 (1993). However, these compounds have not yet been known to serve as intimal hypertrophy inhibitors. Also, analogs of the active ingredients of the present invention, i.e., analogs of the oxindole derivatives, are disclosed in Japanese Patent Application Laid-Open (kokai) Nos. 62-29570, 6-501494, and 7-108900, among which Japanese Patent Application Laid-Open (kokai) Nos. 62-29570 and 6-501494 disclose tyrosine kinase inhibitory activity and Japanese Patent Application Laid-Open (kokai) No. 7-108900 discloses antioxidative action. However, intimal hypertrophy inhibitory action is not at all described in those publications.

Accordingly, the object of the present invention is to provide an excellent intimal hypertrophy inhibiting agent.

DISCLOSURE OF THE INVENTION

Under the above circumstances, the present inventors have conducted careful studies, and have found that oxindole derivatives of a certain class exhibit strong intimal hypertrophy inhibitory activity, leading to completion of the invention.

Accordingly, the present invention provides an intimal hypertrophy inhibitor comprising as the active ingredient an oxindole derivative represented by the following formula (I) or a salt thereof:

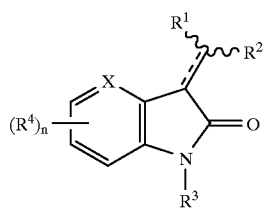

(1)

(wherein R¹ represents a hydrogen atom; a phenyl group which may be substituted by a lower alkyl group, a lower alkoxy group, a lower alkylaminoalkoxy group, a hydroxy group, an amino group, a lower alkylamino group, or a halogen atom; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group; wherein (a) in the case where R¹ is a hydrogen atom:

R² represents a phenyl group which may be substituted by a hydroxyl group or a lower alkoxy group; or a pyridyl group which may be substituted by a lower alkyl group, a lower alkoxy group, a lower alkylaminoalkoxy group, a hydroxyl group, an amino group, a lower alkylamino group, a halogen atom, a lower alkoxycarbonyl group, or a carboxyl group; each of R³ and R⁴ represents a hydrogen atom; X represents CH; and the broken/solid double line denotes a double bond;

(b) in the case where R¹ is a phenyl group which may be substituted by a lower alkyl group, a lower alkoxy group, a lower alkylaminoalkoxy group, a hydroxy group, an amino group, a lower alkylamino group, or a halogen atom; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group:

R² represents a phenyl group which may be substituted by a lower alkyl group, a lower alkoxy group, a lower alkylaminoalkoxy group, a lower alkoxycarbonyl group, a carboxyl group, a hydroxy group, an amino group, a lower alkylamino group, or a halogen atom; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group; R³ represents a hydrogen atom; a lower alkyl group which may be substituted, a benzyl group which may be substituted, a benzenesulfonyl group which may be substituted, or acyl group; R⁴ represents a hydrogen atom, a lower alkoxy group, a halogen atom, an amino group, a carboxyl group, a lower alkylamino group, a lower alkoxycarbonyl group, a phenylcarbamoyl group which may be substituted, or a trifluoromethyl group; X represents CH or N; n represents a number between 0 and 4 inclusive that indicates the number of substituents, and the broken/solid double line denotes a single bond or a double bond).

The present invention also provides a preventive and therapeutic method for intimal hypertrophy, characterized by administering to a patient having intimal hypertrophy the oxindole derivative (1) or a salt thereof.

Moreover, the present invention provides an intimal hypertrophy inhibitor composition characterized by containing the above-described oxindole derivative (1) or a salt thereof and a pharmacologically acceptable carrier.

Furthermore, the present invention provides use of the above-described oxindole derivative (1) or a salt thereof in the preparation of an intimal hypertrophy inhibitor.

BEST MODES FOR CARRYING OUT THE INVENTION

Figure 1:
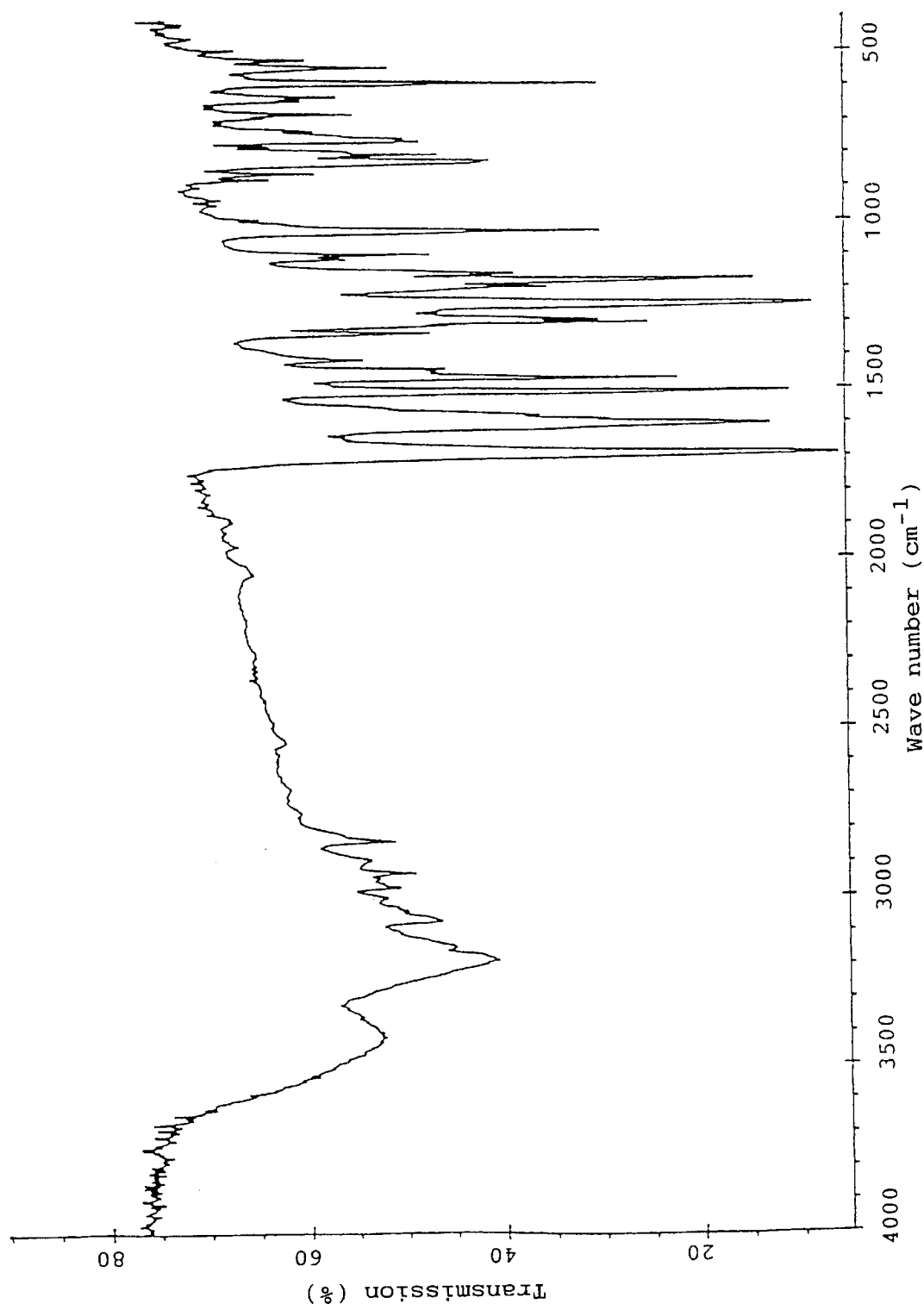
FIG. 1 is a representation of the IR spectrum of the oxindole derivative (Crystal 1) which is used in the present invention.

In the oxindole derivative of formula (1), when the symbol -------- (hereinafter referred to as a broken/solid double line) represents a single bond, there may exist optical isomers due to two asymmetric carbon atoms, whereas when it represents a double bond, geometrical isomers attributed to the double bond exist. The oxindole derivative of the present invention encompasses both types of isomers.

Examples of lower alkyl groups which serve as substituents on the substituted phenyl or pyridyl groups represented by R¹ and R² include linear or branched C1–C6 alkyl groups such as methyl, ethyl, n-propyl, isopropyl, n-butyl, isobutyl, sec-butyl, t-butyl, n-pentyl, isopentyl, and n-hexyl; of which methyl, ethyl, or t-butyl is preferred, and methyl is more preferred. Examples of lower alkoxy groups include linear or branched C1–C6 alkoxy groups such as methoxy, ethoxy, n-propoxy, isopropoxy, n-butoxy, isobutoxy, sec-butoxy, t-butoxy, n-pentyloxy, isopentyloxy, and n-hexyloxy; of which methoxy or ethoxy is preferred, and methoxy is more preferred. Examples of lower alkylaminoalkoxy groups include mono- or di- lower alkylaminoalkoxy groups having C1–C6 alkyl moieties, such as methylaminomethoxy, methylaminoethoxy, methylaminopropoxy, methylaminobutoxy, methylaminopentyloxy, methylaminohexyloxy, ethylaminomethoxy, ethylaminoethoxy, ethylaminopropoxy, n-propylaminomethoxy, n-propylaminoethoxy, n-propylaminopropoxy, dimethylaminomethoxy, dimethylaminoethoxy, dimethylaminopropoxy, dimethylaminobutoxy, dimethylaminopentyloxy, dimethylaminohexyloxy, diethylaminomethoxy, diethylaminoethoxy, diethylaminopropoxy, diethylaminobutoxy, diethylaminopentyloxy, and diethylaminohexyloxy. Of these, preferred are methylaminomethoxy, methylaminoethoxy, dimethylaminomethoxy, dimethylaminoethoxy, ethylaminomethoxy, and ethylaminoethoxy, and more preferred is dimethylaminoethoxy. Examples of lower alkylamino groups include mono- or di- lower alkylamino groups having C1–C4 alkyl moieties, such as methylamino, ethylamino, n-propylamino, i-propylamino, n-butylamino, dimethylamino, diethylamino, and dipropylamino. Of these, dimethylamino is preferred. Examples of halogen atoms include fluorine, chlorine, iodine, or bromine, with chlorine being preferred.

Examples of lower alkoxycarbonyl groups which serve as substituents on the substituted phenyl group represented by R² or on substituted pyridyl groups represented by R¹ and R² include linear or branched C2–C7 alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, and hexyloxycarbonyl; of which methoxycarbonyl and ethoxycarbonyl being preferred.

When $R^1$ or $R^2$ is a substituted phenyl group or a substituted pyridyl group, the number of substituents is preferably between 1 and 3 inclusive. In the case of phenyl rings, the position of substitution may be ortho, meta, or para, and in the case of pyridyl rings, it may be any of 1- through 6- positions. The substituents are preferably lower alkyl groups or lower alkoxy groups, and more preferably methyl or methoxy.

In formula (1), examples of the lower alkyl group which may be substituted and is represented by $R^3$ include those listed above, and examples of substituents on the lower alkyl group include lower alkoxycarbonyl groups, lower alkylamino groups, lower alkylcarbamoyl groups, and carboxyl groups.

Examples of lower alkoxycarbonyl groups include those listed above.

Examples of lower alkylamino groups include mono- or di- lower alkylamino groups having C1–C4 alkyl moieties, such as methylamino, ethylamino, n-propylamino, i-propylamino, n-butylamino, dimethylamino, diethylamino, and dipropylamino.

Examples of lower alkylcarbamoyl groups include carbamoyl groups which are mono- or di-substituted by C1–C6 lower alkyl groups, such as methylcarbamoyl, ethylcarbamoyl, propylcarbamoyl, butylcarbamoyl, pentylcarbamoyl, hexylcarbamoyl, dimethylcarbamoyl, and diethylcarbamoyl, with dimethylcarbamoyl being preferred.

In formula (1), concerning the benzyl group which may be substituted and is represented by $R^3$, examples of substituents on the phenyl ring include lower alkoxy groups and lower alkoxycarbonyl groups. Specific examples are those listed above.

The acyl group represented by $R^3$ in formula (1) broadly encompasses aliphatic acyl groups and aromatic acyl groups, and is exemplified by lower alkanoyl groups, arylcarbonyl groups, heterocyclic carbonyl groups, aryloxycarbonyl groups, lower alkoxycarbonyl groups, and acyloxyacyl groups.

Examples of lower alkanoyl groups include C1–C6 alkanoyl groups such as formyl, acetyl, propionyl, butyryl, isobutyryl, pentanoyl, and hexanoyl.

Examples of arylcarbonyl groups include benzoyl and naphthylcarbonyl groups, and these groups may be substituted by lower alkyl groups, lower alkoxy groups, lower alkoxycarbonyl groups, halogen atoms, carboxyl groups, nitro groups, and cyano groups. Specifically, mention may be given to benzoyl, α-naphthylcarbonyl, β-naphthylcarbonyl, 2-methylbenzoyl, 3-methylbenzoyl, 4-methylbenzoyl, 2,4-dimethylbenzoyl, 4-ethylbenzoyl, 2-methoxybenzoyl, 3-methoxybenzoyl, 4-methoxybenzoyl, 2,4-dimethoxybenzoyl, 4-ethoxybenzoyl, 2-methoxy-4-ethoxybenzoyl, 4-methoxycarbonylbenzoyl, 2,4-dimethoxycarbonylbenzoyl, 4-ethoxycarbonylbenzoyl, 2-chlorobenzoyl, 3-chlorobenzoyl, 4-chlorobenzoyl, 2,3-dichlorobenzoyl, 2-bromobenzoyl, 4-fluorobenzoyl, 2-carboxybenzoyl, 3-carboxybenzoyl, 4-carboxybenzoyl, 2-cyanobenzoyl, 4-cyanobenzoyl, 2-nitrobenzoyl, 4-nitrobenzoyl, or 2,4-dinitrobenzoyl.

Examples of heterocyclic carbonyl groups include 2-furanylcarbonyl, 4-thiazolylcarbonyl, 2-quinolylcarbonyl, 2-pyrazinylcarbonyl, 2-pyridylcarbonyl, 3-pyridylcarbonyl, and 4-pyridylcarbonyl.

Examples of aryloxycarbonyl groups include phenoxycarbonyl, α-naphthyloxycarbonyl, β-naphthyloxycarbonyl, 2-methylphenoxycarbonyl, 3-methylphenoxycarbonyl, 4-methylphenoxycarbonyl, 2,4-dimethylphenoxycarbonyl, 4-ethylphenoxycarbonyl, 2-methoxyphenoxycarbonyl, 3-methoxyphenoxycarbonyl, 4-methoxyphenoxycarbonyl, 2,4-dimethoxyphenoxycarbonyl, 4-ethoxyphenoxycarbonyl, 2-methoxy-4-ethoxyphenoxycarbonyl, 2-chlorophenoxycarbonyl, 3-chlorophenoxycarbonyl, 4-chlorophenoxycarbonyl, 2,3-dichlorophenoxycarbonyl, 2-bromophenoxycarbonyl, 4-fluorophenoxycarbonyl, β-methyl-α-naphthyloxycarbonyl, and β-chloro-α-naphthyloxycarbonyl.

Examples of lower alkoxycarbonyl groups include those listed hereinabove.

Examples of acyloxyacyl groups include acetyloxyacetyl, propionyloxyacetyl, α-(acetyloxy)propionyl, and β-(propionyloxy)propionyl.

On the phenyl ring of each benzenesulfonyl group which may have a substituent and which is represented by $R^3$ in formula (1), substituents may be lower alkyl groups, and specific examples thereof include those listed hereinabove.

Examples of the lower alkoxy groups, halogen atoms, lower alkylamino groups, and lower alkoxycarbonyl groups are those listed hereinabove. Substituents on the phenyl ring of each phenylcarbamoyl group which may have a substituent may be lower alkoxy groups, and specific examples thereof include those listed hereinabove.

Of the oxindole derivatives of formula (1), preferred ones are those described below.

(a') In the case where $R^1$ is a hydrogen atom:
   $R^2$ is preferably a phenyl group which may be substituted by a hydroxy group or a lower alkoxy group; or a pyridyl group which may be substituted by a lower alkoxy group; each of $R^3$ and $R^4$ represents a hydrogen atom; X represents CH; and the broken/solid double line denotes a double bond; wherein $R^2$ is more preferably pyridyl, 4-methoxyphenyl, or 3,5-dimethoxy-4-hydroxyphenyl.

(b') in the case where $R^1$ is a not a hydrogen atom:
   $R^1$ and $R^2$ may be identical to or different from each other, and each of $R^1$ and $R^2$ is preferably a phenyl group which may be substituted by a lower alkyl group, a lower alkoxy group, a lower alkylaminoalkoxy group, a hydroxy group, an amino group, a lower alkylamino group, or a halogen atom; or a pyridyl group which may be substituted by a lower alkoxy group; $R^3$ represents a hydrogen atom; a lower alkyl group which may be substituted by a lower alkoxycarbonyl group, a lower alkyl amino group, or a lower alkylcarbamoyl group; a benzyl group which may be substituted, on the phenyl ring, by a lower alkoxy group or a lower alkoxycarbonyl group; a benzoyl group which may be substituted, on the phenyl ring, by a lower alkoxy group; or a benzenesulfonyl group which may be substituted, on the phenyl ring, by a lower alkyl group; and $R^4$ represents a hydrogen atom, an amino group, a carboxyl group, a lower alkylamino group, or a lower alkoxycarbonyl group. More preferably, $R^1$ and $R^2$ are identical to or different from each other, and each represents a pyridyl group; or a phenyl group which may be substituted by methyl, ethyl, butyl, methoxy, hydroxy, amino, dimethylamino, dimethylaminoethoxy, or chlorine; R³ represents a hydrogen atom; a lower alkyl group which may be substituted by methoxycarbonyl, ethoxycarbonyl, dimethylamino, or dimethylcarbamoyl; a benzyl group which may be substituted, on the phenyl ring, by a methoxycarbonyl group; or a benzenesulfonyl group which may be substituted, on the phenyl ring, by a methyl group; and R⁴ represents a hydrogen atom, an amino group, a carboxyl group, a di- lower alkylamino group, or a lower alkoxycarbonyl group; X represents CH; and the broken/solid double line represents a double bond. Particularly preferred are compounds in which R¹ or R² is pyridyl, phenyl, tolyl, butylphenyl, methoxyphenyl, hydroxyphenyl, or dimethylaminoethoxyphenyl; R³ is a hydrogen atom, a methyl group, a methoxycarbonylpentyl group, an ethoxycarbonylmethyl group, a dimethylaminoethyl group, a dimethylcarbamoylmethyl group, a methoxycarbonylbenzyl group, or a toluenesulfonyl group; R⁴ is a hydrogen atom, an amino group, a carboxyl group, a dimethylamino group, or an ethoxycarbonyl group; X represents CH; n represents 1 or 2; and the broken/solid double line represents a double bond.

The oxindole derivatives of formula (1) of the present invention may be prepared in accordance with the synthesis method described, for example, Japanese Patent Publication (kokoku) 43-3195, Japanese Patent Application Laid-Open (kokai) No. 47-8628, WO 91/01306, and WO 92/07830. For example, they can be prepared in accordance with the following reaction scheme.

(wherein R¹, R², R³, R⁴, X, and n have the same meanings as defines above; R³ᵃ represents a lower alkyl, benzyl, or benzenesulfonyl group, each of which may have a substituent, or an acyl group; and Z represents a halogen atom).

Examples of the halogen atom represented by Z in the above-described reaction scheme are listed hereinabove, and preferably, the halogen atom is a chlorine atom.

Step A

A known compound represented by formula (2) and another known compound represented by (3) are reacted in a suitable solvent in the presence of a condensing agent, to thereby yield a compound of formula (1a). The solvent is not particularly limited so long as it does not affect the reaction, and examples thereof include toluene, tetrahydrofuran, dimethylformamide, dimethylsulfoxide, dioxane, acetic acid, t-amyl alcohol, and t-butyl alcohol. Examples of the condensing agent include inorganic bases such as sodium hydride, sodium hydroxide, potassium hydroxide, sodium hydrogencarbonate, potassium carbonate, and sodium carbonate; organic bases such as triethylamine, piperazine, piperidine, pyrrolidine, pyridine, and potassium-t-butoxide; ammonium acetate; and sodium acetate. The reaction is preferably carried out using 1–3 moles of the formula (3) compound and 1–10 moles of a condensing agent with respect to 1 mole of the formula (2) compound. The reaction temperature is preferably between room temperature and 200° C., and the reaction time is preferably 1–24 hours.

The compounds represented by formula (2) may be prepared in accordance with the methods described, for

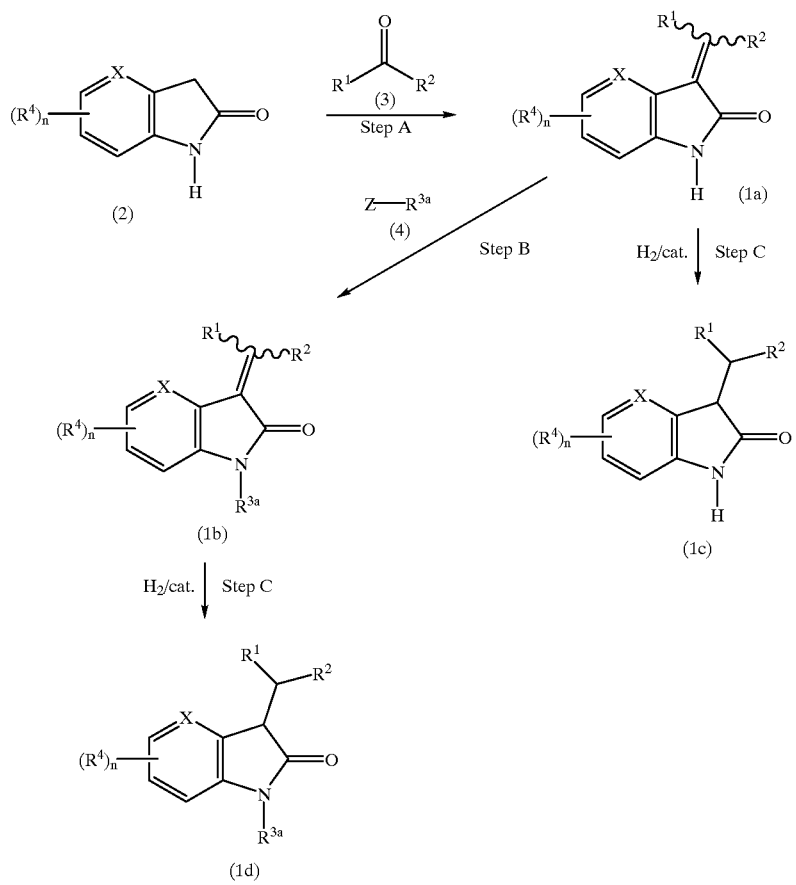

example, in Journal of Medicinal Chemistry, 37, 2033 (1994), Tetrahedron Letters, 2587 (1979), Journal of American Chemical Society, 5508 (1974), Journal of American Society, 5512 (1974), Tetrahedron, 24, 6093 (1968), or Japanese Patent Application Laid-Open (kokai) No. 4-210981. The compounds represented by formula (3) may be prepared in accordance with the methods described, for example, in Organic Synthesis Collection, vol. I, $p^{95}$, Journal of Chemical Society, 529 (1951), Monatsh. Chem., 119, 1427 (1988), Rec. Trav. Chim. Pays-Bas Belg., 70, 1054 (1951).

Step B

Compound of formula (1a) obtained in Step A is reacted with a known compound represented by (4) in a suitable solvent in the presence of a base, to thereby yield the target compound of formula (1b). The solvent is not particularly limited so long as it does not affect the reaction, and examples thereof include dimethylformamide, dimethylsulfoxide, tetrahydrofuran, and dioxane. Examples of the base include sodium hydride, sodium hydrogencarbonate, potassium carbonate, and sodium carbonate. The reaction is preferably carried out using 1–3 moles of the formula (4) compound and 1–3 moles of a base with respect to 1 mole of the formula (1a) compound. The reaction temperature is between room temperature and 100° C., and the reaction time is preferably 1–24 hours.

Step C

When the compound of formula (1a) obtained in Step A or the compound of formula (1b) obtained in Step B is subjected to catalytic hydrogenation in a suitable solvent, in the presence of a suitable catalyst, and in a hydrogen stream, a compound of formula (1c) or (1d) is obtained. The solvent is not particularly limited so long as it does not affect the reaction, and examples thereof include tetrahydrofuran, dioxane, benzene, toluene, methanol, ethanol, ethyl acetate, and acetic acid. Examples of the catalyst include palladium, palladium-on-carbon, rhodium, platinum, and ruthenium. The reaction is preferably carried out using 0.01–0.1 moles of a catalyst with respect to 1 mole of the formula (1a) or (1b) compound. The hydrogen stream is preferably 1–3 atm. The reaction temperature is around room temperature, and the reaction time is preferably between 10 minutes and 24 hours.

Of the compounds of formula (1) obtained in the above steps, the compounds in which $R^1$ or $R^2$ is a phenyl group substituted by a carboxyl group may be transformed by known methods so as to esterify the carboxyl group on the phenyl ring.

The formula (1) compound obtained in accordance with the above reaction scheme may be easily separated as crystals or oily matter by routine separation/purification means such as recrystallization, distillation, column chromatography, etc.

Moreover, through customary methods, the compound of formula (1) may be transformed into salts of physiologically acceptable acids or bases, including salts obtained from reaction with inorganic acids such as hydrochloric acid, sulfuric acid, or nitric acid; salts obtained from reaction with organic acids such as acetic acid, oxalic acid, succinic acid, or maleic acid; salts obtained from reaction with alkali metals such as sodium and potassium; and salts obtained from reaction with alkaline earth metals such as calcium. The resultant formula (1) compounds may also be used in the form of solvates typified by hydrates.

The intimal hypertrophy inhibitors of the present invention may be formed into drug preparations by routine methods through use of suitable pharmaceutical carriers. There may be incorporated a variety of carriers—such as vehicles, binders, disintegrators, lubricants, colorants, flavoring agents, odor-improvers, and surfactants—that are widely used in common drugs.

When the intimal hypertrophy inhibitor of the present invention is used as a remedy for mammals including humans, the form of administration unit of the drug is not particularly limited, and is suitably selected in accordance with the therapeutic purposes. Specifically, mention may be given of parenteral forms such as injections, suppositories, topical agents (ointments, patches, etc.), and aerosols; and peroral forms such as tablets, coated tablets, powders, granules, capsules, liquids, pills, suspensions, and emulsions.

The above-described various drugs are prepared by drug preparation methods well known in the art.

When solid preparations for peroral use—such as tablets, powders, and granules—are prepared, there may be used vehicles such as lactose, sucrose, sodium chloride, glucose, urea, starch, calcium carbonate, kaolin, crystalline cellulose, silicic acid, methylcellulose, glycerol, sodium alginate, and gum arabic; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, hydroxypropylcellulose, water, ethanol, and potassium phosphate; disintegrators such as dry starch, sodium alginate, agar powder, laminaran powder, sodium hydrogencarbonate, calcium carbonate, polyoxyethylene sorbitan aliphatic esters, sodium lauryl sulfate, stearic monoglyceride, starch, and lactose; anti-disintegrators such as sucrose, stearic acid, cacao butter, and hydrogenated oils; absorption improvers such as quaternary ammonium bases and sodium lauryl sulfate; humectants such as glycerol and starch; adsorbing agents such as starch, lactose, kaolin, bentonite, and colloidal silica; and lubricants such as purified talc, stearates, boric acid powder, and polyethylene glycol. If desired, tablets may have customary coatings such as sugar coating, gelatin coating, enteric coating, film coating, double coating, and multiple coating.

When pills are formed, there may be used carriers including vehicles such as glucose, starch, cacao butter, hydrogenated vegetable oils, kaolin, and talc; binders such as gum arabic powder, tragacanth gum powder, gelatin, and ethanol; and disintegrants such as laminaran and agar powder.

Capsules are prepared through mixing the compound with the aforementioned various carriers, and then packing the mixture into hard gelatin capsules, soft capsules, etc.

When suppositories are prepared, carriers such as polyethylene glycol, cacao butter, lanolin, higher alcohols, esters of higher alcohols, gelatin, semisynthesized glycerides, or Witepsole (registered trademark, Dynamite-Nobel) are used in combination with suitable absorption promoters.

When injection preparations are prepared, there may be used various carriers including diluents such as water, ethyl alcohol, macrogol, propylene glycol, ethoxylated isostearyl alcohol, polyoxyisostearic alcohol, and polyoxyethylene sorbitan aliphatic esters; pH regulators and buffers such as sodium citrate, sodium acetate, and sodium phosphate; and stabilizers such as sodium pyrosulfite, ethylenediaminetetraacetic acid, thioglycolic acid, and thiolactic acid. In this case, the pharmaceutical compositions may also contain NaCl, glucose, or glycerol in suitable amounts sufficient to prepare a isotonic solution. Moreover, ordinary solution adjuvants, soothing agents, and local analgesics may additionally be incorporated. Subcutaneous, intramuscular, and intravenous injection preparations are prepared by use of these carriers in customary methods.

Liquid preparations may be aqueous or oily suspension, solutions, syrups, or elixirs, which are prepared in accordance with customary methods using common additives.

When ointments, e.g., pastes, creams, or gels are prepared, commonly used bases, stabilizers, humectants, preservatives, etc. are incorporated as required, after which the ingredients are mixed to form drug preparations in accordance with customary methods. Examples of bases include white Vaseline, paraffin, glycerol, cellulose derivatives, polyethyleneglycol, silicone, bentonite, etc. Examples of preservatives include methyl paraoxybenzoate, ethyl paraoxybenzoate, and propyl paraoxybenzoate.

When patches are prepared, the aforementioned ointments, creams, gels, pastes, etc. are applied onto conventionally-known supports through use of customary methods. Examples of suitable supports include woven or non-woven fabrics made of cotton, staple fiber, or chemical fiber; and films and foamed sheets made of soft vinyl chloride, polyethylene, polyurethane, etc.

The amount of the compound of the present invention to be incorporated into any of the above-described preparations varies in accordance with the form of preparation, administration route, and dosage regimen, and is suitably determined within a wide range. However, it is advisable that the compound be incorporated in an amount of 1–70% by weight based on the total weight of the preparation.

The route of administration, which is not particularly limited, is suitably determined in accordance with the form of preparation; age, sex, and other conditions of the patient; severity of the patient's symptoms, etc. For example, parenteral administration, peroral administration, rectal administration, administration in the oral cavity, and transdermal administration may be suitably used. Tablets, pills, liquids, suspensions, emulsions, granules, and capsules are orally administered; and suppositories are inserted into the rectum. Injection preparations may be intravenously administered in their own forms or in combination with commonly used adjuvants such as glucose and amino acids. When necessary, injection preparations are used singly for purposes of intraarterial, intramuscular, intracutaneous, subcutaneous, or intraperitoneal administrations. Ointments are applied onto the skin, mouth mucosa, etc.

The amount of the active ingredient of the present invention to be administered is suitably determined in accordance with the manner of administration; age, sex, and pathological conditions of the patient; identity of the compound of the present invention; and other factors. However, usually it is to be determined within the yardstick range of 0.1–300 mg/kg/day, preferably 0.5–100 mg/kg/day. The drug preparations of the present invention may be administered in a single administration or 2–4 divided administrations per day.

EXAMPLES

The present invention will be explained in more detail by the following examples, which are provided merely for illustration purposes and therefore should not be construed as limiting the present invention.

Preparation Example 1

Synthesis of 3-[bis(4-methoxyphenyl)methylene]-oxindole (Compound 1)

10.0 g of oxindole was dissolved in 100 ml tetrahydrofuran, and 21.8 g of 4,4'-dimethoxybenzophenone was added thereto at room temperature. Subsequently, the temperature of the reaction was brought to 0° C. 9.0 g of 60% sodium hydride was added, and when generation of hydrogen ceased, the reaction mixture was refluxed with heat for 12 hours. After completion of reaction, the reaction mixture was cooled. Saturated aqueous ammonium chloride solution was added, followed by extraction with ethyl acetate. The extract was washed with water and saturated brine, dried over sodium sulfate, and then evaporated. The resultant crude product was recrystallized from methanol, to thereby obtain 22.8 g (yield 85%) of the title compound in yellow crystals (Crystal 1). The melting point and elementary analysis data are shown in Table 1, and NMR and MS spectrum data are shown in Table 2. Also, the IR spectrum chart of the compound is shown in FIG. 1.

Figure 2:
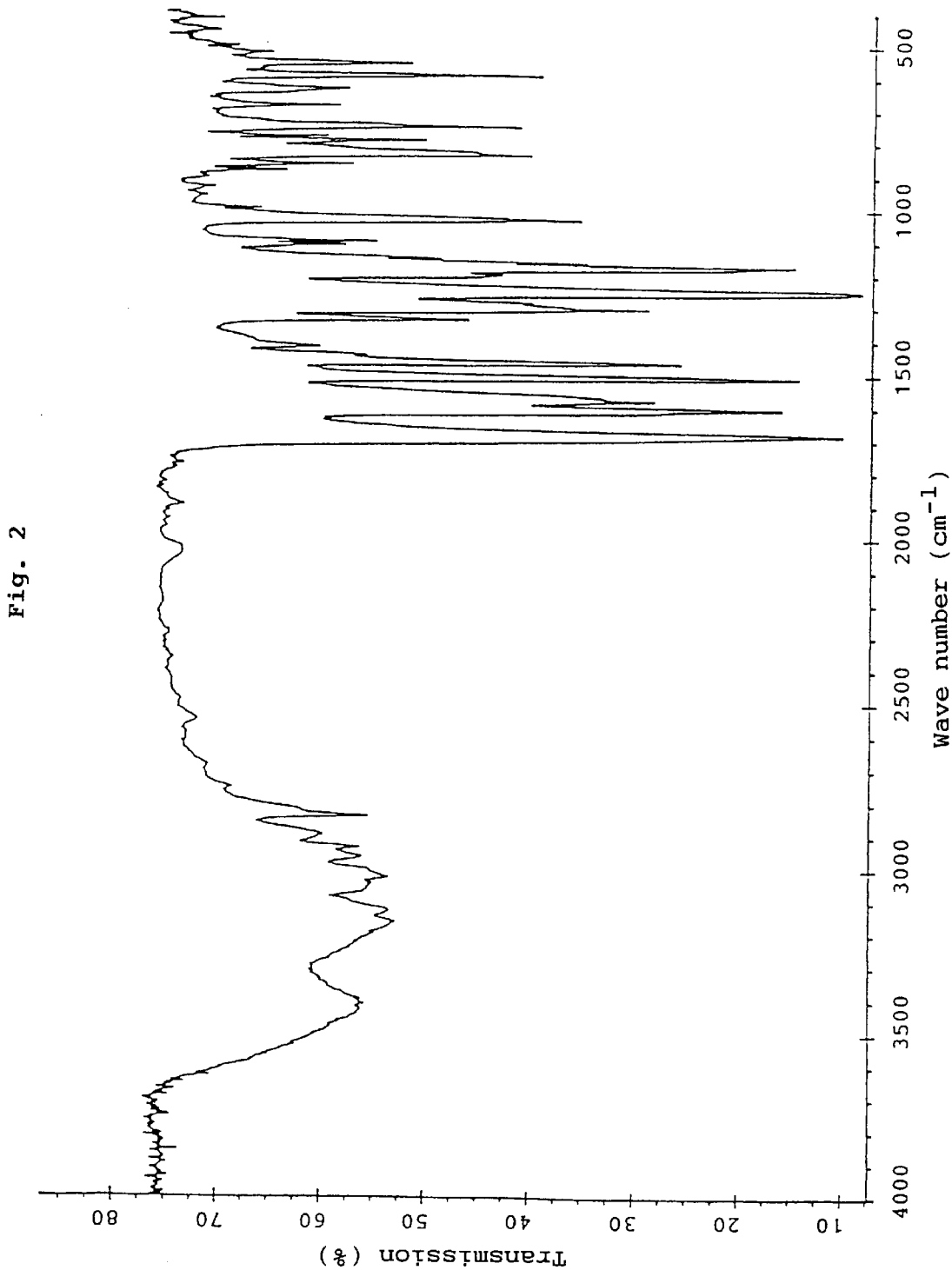
FIG. 2 is a representation of the IR spectrum of the oxindole derivative (Crystal 2) which is used in the present invention.

20 g of the compound (Crystal 1) obtained in Preparation Example 1 was suspended in 200 ml n-undecane. The suspension was heated for 4 hours at approximately 160° C. and then cooled to 0° C., to thereby obtain 19.6 g (yield 98%) of orange-colored polymorphic crystals (Crystal 2) of Compound 1. FIG. 2 shows the IR spectrum chart of the compound. The melting point was 203.5–205.5° C.

Preparation Example 2

Suitable starting materials were used in a method similar to that of Preparation Example 1, to thereby synthesize Compounds 2 through 15 shown in Tables 1–4.

TABLE 1

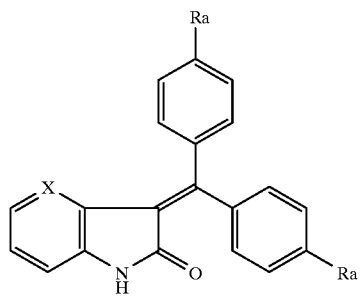

| Compound | Ra | X | m.p. (°C.) | | Elementary Anal. (%) | | |
|---|---|---|---|---|---|---|---|
| | | | | | C | H | N |
| 1 (Crystal 1) | OMe | CH | 176~179 | Calc. | 77.29 | 5.36 | 3.92 |
| | | | | Found | 77.32 | 5.23 | 3.93 |
| 2 | Me | CH | 240~241 | Calc. | 84.89 | 5.89 | 4.30 |
| | | | | Found | 85.00 | 5.75 | 4.24 |
| 3 | t-Bu | CH | 255~258 | Calc. | 85.05 | 7.63 | 3.42 |
| | | | | Found | 84.89 | 7.70 | 3.37 |
| 4 | Cl | CH | 206~208 | Calc. | 68.87 | 3.58 | 3.82 |
| | | | | Found | 69.09 | 3.29 | 3.79 |
| 5 | OH | CH | 300 (decomp.) | Calc. | 74.54 | 4.77 | 4.14 |
| | | | | Found | 74.55 | 4.55 | 4.03 |
| 6 (+2HCl, 7H$_2$O) | OCH$_2$CH$_2$NMe$_2$ | CH | amorphas | Calc. | 51.94 | 7.36 | 6.27 |
| | | | | Found | 51.89 | 7.17 | 5.88 |
| 7 | H | CH | 236~237 | Calc. | 83.81 | 5.16 | 4.65 |
| | | | | Found | 83.60 | 4.84 | 4.64 |
| 8 (+1/4H$_2$O) | OMe | N | amorphas | Calc. | 72.81 | 5.14 | 7.72 |
| | | | | Found | 72.99 | 5.43 | 7.43 |

TABLE 2

| Comp. | N. M. R(δ ppm)/solv. | M. S. |
|---|---|---|
| 1 | 3.84(s, 3H), 3.88(s, 3H), 6.51(d, 1H), 6.65(t, 1H), 6.70(d, 1H), 6.87(d, 2H), 6.93(d, 2H), 7.04(t, 1H), 7.25(d, 2H), 7.31(d, 2H), 8.40(s, 1H)/CDCl$_3$ | 357 (EI$^+$) |
| 2 | 2.37(s, 3H), 2.43(s, 3H), 6.47(d, 1H), 6.65(t, 1H), 6.73(d, 1H), 7.07(t, 1H), 7.13~7.26(m, 8H), 7.79(s, 1H)/CDCl$_3$ | 325 (EI$^+$) |
| 3 | 1.33(s, 9H), 1.38(s, 9H), 6.37(d, 1H), 6.64(t, 1H), 6.74(d, 1H), 7.07(t, 1H), 7.21~7.44(m, 8H), 7.71(brs, 1H)/CDCl$_3$ | 409 (EI$^+$) |
| 4 | 6.47(d, 1H), 6.70(d, 1H), 6.72(d, 1H), 7.13(t, 1H), 7.25(d, 2H), 7.32(d, 2H), 7.33(d, 2H), 7.42(d, 2H), 8.05(s, 1H)/CDCl$_3$ | 366 (FAB$^+$) |
| 5 | 6.29(d, 1H), 6.59(t, 1H), 6.69(d, 1H), 6.72(d, 1H), 6.84(d, 2H), 6.99~7.10(m, 6H), 9.79(brs, 1H), 9.91(brs, 1H), 10.33(s, 1H)/DMSO-d$_6$ | 329 (EI$^+$) |
| 6 | 2.34(s, 6H), 2.37(s, 6H), 2.75(m, 4H), 4.12(m, 4H), 6.50(d, 1H), 6.66(t, 1H), 6.75(d, 1H), 6.87(d, 2H), 6.94(d, 2H), 7.06(t, 1H), 7.23(d, 2H), 7.29(d, 2H), 8.07(brs, 1H)/CDCl$_3$ | 471 (EI$^+$) |
| 7 | 6.37(d, 1H), 6.64(t, 1H), 6.69(d, 1H), 7.07(t, 1H), 7.30~7.45(m, 10H), 8.26(s, 1H)/CDCl$_3$ | 298 (FAB$^+$) |
| 8 | 3.86(s, 3H), 3.87(s, 3H), 6.92(m, 6H), 7.32(m, 5H), 8.04(m, 1H)/CDCl$_3$ | |

TABLE 3

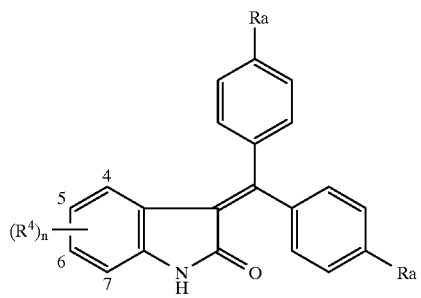

| Compound | $(R^4)_n$ | Ra | m.p. (°C.) | | Elementary Anal. (%) | | |
|---|---|---|---|---|---|---|---|
| | | | | | C | H | N |
| 9 | 5-CO$_2$Et | Me | 236~237 | Calc. | 78.57 | 5.83 | 3.52 |
| | | | | Found | 78.67 | 5.79 | 3.26 |
| 10 (+1/2H$_2$O) | 5-NMe$_2$ | OMe | 164~166 | Calc. | 73.33 | 6.15 | 6.84 |
| | | | | Found | 73.15 | 5.91 | 6.90 |
| 11 | 5-F | OMe | 178~179 | Calc. | 73.59 | 4.83 | 3.73 |
| | | | | Found | 73.75 | 4.67 | 3.74 |
| 12 | 5-CF$_3$ | H | 225~226 | Calc. | 72.33 | 3.86 | 3.83 |
| | | | | Found | 72.42 | 3.60 | 3.83 |
| 13 (+H$_2$O) | 6-NH$_2$ | Me | 248~250 | Calc. | 77.07 | 6.19 | 7.82 |
| | | | | Found | 76.78 | 5.85 | 7.56 |
| 14 | 5,6-(OMe)$_2$ | OMe | 200~202 | Calc. | 71.93 | 5.55 | 3.36 |
| | | | | Found | 71.89 | 5.63 | 3.25 |
| 15 (+1/10H$_2$O) | (5-(p-MeO—C$_6$H$_4$—NHCO) | Me | 244~246 | Calc. | 78.17 | 5.54 | 5.88 |
| | | | | Found | 78.09 | 5.44 | 5.82 |

TABLE 4

| Comp. | N. M. R(δ ppm)/solv. | M. S. |
|---|---|---|
| 9 | 1.24(t, 3H), 2.38(s, 3H), 2.44(s, 3H), 4.18(q, 2H), 6.60(d, 1H), 7.17(d, 2H), 7.19(d, 2H), 7.23(d, 2H), 7.27(d, 2H), 7.28(s, 1H), 7.78(d, 1H), 8.96(s, 1H)/CDCl$_3$ | 397 (EI$^+$) |
| 10 | 2.59(s, 6H), 3.84(s, 3H), 3.85(s, 3H), 6.02(s, 1H), 6.55(d, 1H), 6.63(d, 1H), 6.85(d, 2H), 6.95(d, 2H), 7.28(d, 2H), 7.33(d, 2H), 7.48(brs, 1H)/CDCl$_3$ | 400 (EI$^+$) |
| 11 | 3.85(s, 3H), 3.89(s, 3H), 6.23(d, 1H), 6.66(d, 1H), 6.78(t, 1H), 6.87(d, 2H), 6.95(d, 2H), 7.23(d, 2H), 7.30(d, 2H), 7.65(s, 1H)/CDCl$_3$ | 376 (FAB$^+$) |
| 12 | 6.53(s, 1H), 6.71(d, 1H), 7.25~7.51(m, 11H), 8.64(brs, 1H)/CDCl$_3$ | 365 (EI$^+$) |
| 13 | 2.30(s, 3H), 2.37(s, 3H), 3.38(m, 2H), 6.00(m, 2H), 6.21(s, 1H), 7.07(s, 4H), 7.09(d, 2H), 7.25(d, 2H), 10.24(s, 1H)/DMSO-d$_6$ | 340 (EI$^+$) |
| 14 | 3.44(s, 3H), 3.82(s, 6H), 3.85(s, 3H), 6.04(s, 1H), 6.35(s, 1H), 6.86(d, 2H), 6.95(d, 2H), 7.26~7.36 (m,4H), 7.65(s, 1H)/CDCl$_3$ | 418 (FAB$^+$) |
| 15 | 2.33(s, 3H), 2.35(s, 3H), 3.72(s, 3H), 6.83~6.95 (m, 4H), 7.14(s, 4H), 7.16(d, 2H), 7.29(d, 2H), 7.52 (d, 2H), 7.70(d, 1H), 9.70(s, 1H), 10.74(s, 1H)/DMSO-d$_6$ | 474 (EI$^+$) |

Preparation Example 3
Synthesis of 1-dimethylaminoethyl-3-[bis(4-methoxyphenyl)methylene]oxindole.HCl (Compound 16)

5.0 g of 3-[bis(4-methoxyphenyl)methylene]oxindole obtained in Preparation Example 1 was dissolved in 50 ml tetrahydrofuran, and 4.0 g of dimethylaminoethylchloride-HCl was added thereto at room temperature. Subsequently, the temperature of the reaction was brought to 0° C. 2.2 g of 60% sodium hydride was added, and when generation of hydrogen ceased, the reaction mixture was refluxed with heat for 12 hours. After completion of reaction, the reaction mixture was cooled. Saturated aqueous ammonium chloride solution was added, followed by extraction with ethyl acetate. The extract was washed with water and saturated brine, dried over sodium sulfate, and then evaporated. The resultant crude product was purified by silica gel column chromatography (chloroform:methanol=100:1), to thereby obtain yellow crystals. When the crystals were processed with 4 N HCl/ethyl acetate solution, 4.6 g (yield 70%) of the title compound was obtained in yellow crystals. The melting point and elementary analysis data are shown in Table 5, and NMR and MS spectrum data are shown in Table 6.

Preparation Example 4

Suitable starting materials were used in a method similar to that of Preparation Example 3, to thereby synthesize Compounds 17 through 24 shown in Tables 5 and 6.

TABLE 5

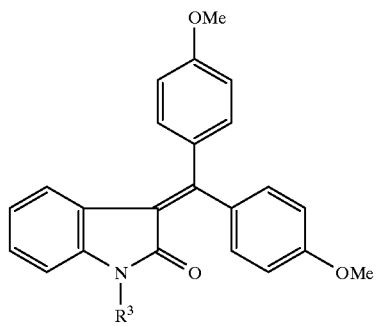

| Compound | R³ | m.p. (°C.) | | Elementary Anal. (%) | | |
|---|---|---|---|---|---|---|
| | | | | C | H | N |
| 16 (+HCl) | CH₂CH₂NMe₂ | 217~221 | Calc. | 69.74 | 6.29 | 6.02 |
| | | | Found | 69.46 | 6.44 | 5.89 |
| 17 | Me | 201~203 | Calc. | 77.61 | 5.70 | 3.77 |
| | | | Found | 77.66 | 5.64 | 3.72 |
| 18 (+1/2H₂O) | CH₂CO₂Et | amorphas | Calc. | 71.67 | 5.79 | 3.10 |
| | | | Found | 71.90 | 5.65 | 3.09 |
| 19 (+1/3H₂O) | CH₂CO₂H | 206~209 | Calc. | 71.25 | 5.18 | 3.32 |
| | | | Found | 71.23 | 5.20 | 3.18 |
| 20 (+1/6H₂O) | CH₂CONMe₂ | 207~208 | Calc. | 72.79 | 5.96 | 6.29 |
| | | | Found | 72.79 | 5.77 | 6.15 |
| 21 (+1/2H₂O) | n-Bu | oil | Calc. | 76.25 | 6.68 | 3.32 |
| | | | Found | 76.71 | 6.40 | 3.02 |
| 22 | (CH₂)₅CO₂Et | oil | Calc. | 74.53 | 6.66 | 2.80 |
| | | | Found | 74.31 | 6.79 | 2.83 |
| 23 | p-MeO—C₆H₄—CH₂ | amorphas | Calc. | 77.97 | 5.70 | 2.93 |
| | | | Found | 77.89 | 5.69 | 2.85 |
| 24 | p-MeO₂C—C₆H₄—CH₂ | amorphas | Calc. | 76.02 | 5.38 | 2.77 |
| | | | Found | 76.01 | 5.31 | 2.76 |

TABLE 6

| Comp. | N. M. R(δ ppm)/solv. | M. S. |
|---|---|---|
| 16 | 2.84(s, 6H), 3.34(m, 2H), 3.80(s, 3H), 3.84(s, 3H), 4.10(t, 2H), 6.37(d, 1H), 6.73(t, 1H), 6.89(d, 2H), 7.05(d, 2H), 7.16~7.26(m, 6H), 10.54(brs, 1H)/DMSO-d₆ | 429 (FAB⁺) |
| 17 | 3.22(s, 3H), 3.84(s, 3H), 3.88(s, 3H), 6.56(d, 1H), 6.70(t, 1H), 6.77(d, 1H), 6.88(d, 2H), 6.93(d, 2H), 7.14(t, 1H), 7.25(d, 2H), 7.28(d, 2H)/CDCl₃ | 372 (FAB⁺) |
| 18 | 1.26(t, 3H), 3.84(s, 3H), 3.88(s, 3H), 4.21(q, 2H), 4.49(s, 2H), 6.60(d, 1H), 6.66(d, 1H), 6.72(t, 1H), 6.87(d, 2H), 6.94(d, 2H), 7.12(t, 1H), 7.25~7.31 (m, 4H)/CDCl₃ | 444 (FAB⁺) |
| 19 | 3.82(s, 3H), 3.88(s, 3H), 4.52(s, 2H), 6.60(d, 1H), 6.69(d, 1H), 6.73(t, 1H), 6.86(d, 2H), 6.93(d, 2H), 7.12(t, 1H), 7.26(d, 2H), 7.29(d, 2H), 8.89(brs, 1H)/CDCl₃ | 416 (FAB⁺) |
| 20 | 2.95(s, 3H), 3.07(s, 3H), 3.83(s, 3H), 3.88(s, 3H), 4.55(s, 2H), 6.58(d, 1H), 6.70(t, 1H), 6.83(d, 1H), 6.87(d, 2H), 6.93(d, 2H), 7.11(t, 1H), 7.28(m, 4H)/CDCl₃ | 442 (EI⁺) |
| 21 | 0.94(t, 3H), 1.39(six, 2H), 1.66(quint, 2H), 3.72(t, 2H), 3.83(s, 3H), 3.88(s, 3H), 6.55(d, 1H), 6.68(t, 1H), 6.78(d, 1H), 6.87(d, 2H), 6.96(d, 2H), 7.25(d, 2H), 7.29(d, 2H)/CDCl₃ | 413 (EI⁺) |
| 22 | 1.23(t, 3H), 1.40(m, 2H), 1.66(m, 4H), 2.28(t, 2H), 3.72(t, 2H), 3.84(s, 3H), 3.88(s, 3H), 4.11(q, 2H), 6.56(d, 1H), 6.69(d, 1H), 6.77(d, 1H), 6.87(d, 2H), 6.93(d, 2H), 7.12(t, 1H), 7.25(d, 2H), 7.28(d, 2H)/CDCl₃ | 499 (EI⁺) |
| 23 | 3.75(s, 3H), 3.83(s, 3H), 3.87(s, 3H), 4.87(s, 2H), 6.54(d, 1H), 6.67(m, 2H), 6.82(d, 2H), 6.89(d, 2H), 6.92(d, 2H), 7.02(t, 1H), 7.26(d, 2H), 7.27(d, 2H), 7.32(d, 2H)/CDCl₃ | 478 (FAB⁺) |

TABLE 6-continued

| Comp. | N. M. R(δ ppm)/solv. | M. S. |
|---|---|---|
| 24 | 3.84(s, 3H), 3.88(s, 3H), 3.89(s, 3H), 4.99(s, 2H), 6.60(m, 2H), 6.68(t, 1H), 6.89(d, 2H), 6.94(d, 2H), 7.02(t, 1H), 7.27(d, 2H), 7.33(d, 2H), 7.39(d, 2H), 7.97(d, 2H)/CDCl₃ | 505 (EI⁺) |

Preparation Example 5

Synthesis of 1-paratoluenesulfonyl-3-[bis(4-methoxyphenyl)methylene]oxindole (Compound 25)

5.0 g of 3-[bis(4-methoxyphenyl)methylene]oxindole obtained in Preparation Example 1 was dissolved in 50 ml tetrahydrofuran, and 3.2 g of paratoluenesulfonyl chloride was added thereto at room temperature. Subsequently, the temperature of the reaction was brought to 0° C. 2.2 g of 60% sodium hydride was added, and when generation of hydrogen ceased, the reaction mixture was refluxed with heat for 12 hours. After completion of reaction, the reaction mixture was cooled. Saturated aqueous ammonium chloride solution was added, followed by extraction with ethyl acetate. The extract was washed with water and saturated brine, dried over sodium sulfate, and then evaporated. The resultant crude product was recrystallized from methanol, to thereby obtain 3.9 g (yield 60%) of the title compound in the form of yellow crystals. The melting point and elementary analysis data are shown in Table 7, and NMR and MS spectrum data are shown in Table 8.

Preparation Example 6

Suitable starting materials were used in a method similar to that of Preparation Example 5, to thereby synthesize Compound 26 shown in Tables 7 and 8.

TABLE 7

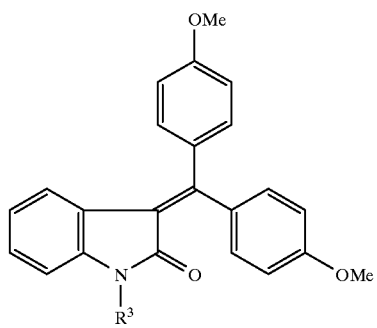

| Compound | R³ | m.p. (°C.) | | Elementary Anal. (%) | | |
|---|---|---|---|---|---|---|
| | | | | C | H | N |
| 25 | p-Me—C₆H₄—SO₂ | 166~167 | Calc. | 70.43 | 4.93 | 2.74 |
| | | | Found | 70.59 | 4.82 | 2.70 |
| 26 | p-MeO₂C—C₆H₄—CO | 210~211 | Calc. | 73.98 | 4.85 | 2.70 |
| | | | Found | 73.81 | 4.68 | 2.74 |

TABLE 8

| Comp. | N. M. R(δ ppm)/solv. | M. S. |
|---|---|---|
| 25 | 2.40(s, 3H), 3.83(s, 3H), 3.86(s, 3H), 6.55(d, 1H), 6.77~6.92(m, 5H), 7.13~7.28(m, 7H), 7.97(m, 3H)/CDCl₃ | 512 (FAB⁺) |
| 26 | 3.79(s, 3H), 3.90(s, 3H), 3.93(s, 3H), 6.68(d, 1H), 6.80(d, 2H), 6.88(t, 1H), 6.95(d, 2H), 7.19~7.27 (m, 5H), 7.76(d, 2H), 7.88(d, 1H), 8.07(d, 2H)/CDCl₃ | 519 (EI⁺) |

Preparation Example 7

Synthesis of 3-[bis(4-methoxyphenyl)methyl]oxindole (Compound 27)

5.0 g of 3-[bis(4-methoxyphenyl)methylene]oxindole obtained in Preparation Example 1 was dissolved in 100 ml methanol, and the solution was catalytically reduced through use of 10% palladium-on-carbon for 12 hours at room temperature under 3 atm hydrogen. After completion of reaction, the catalyst was removed by filtration through cerite, and the filtrate was evaporated under reduced pressure and then cooled. The resultant crude product was purified by silica gel column chromatography (ethyl acetate:n-hexane=100:1), to thereby obtain 5.1 g (yield 100%) of the title compound in the form of white crystals. The melting point and elementary analysis data are shown in Table 9, and NMR and MS spectrum data are shown in Table 10.

Preparation Example 8

Suitable starting materials were used in a method similar to that of Preparation Example 7, to thereby synthesize Compound 28 shown in Tables 9 and 10.

TABLE 9

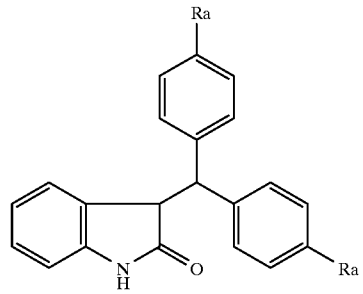

| Compound | Ra | m.p. (°C.) | | Elementary Anal. (%) | | |
|---|---|---|---|---|---|---|
| | | | | C | H | N |
| 27 | MeO | 180~181 | Calc. | 76.86 | 5.89 | 3.90 |
| | | | Found | 76.74 | 5.82 | 3.86 |
| 28 | Me | 190~191 | Calc. | 84.37 | 6.46 | 4.28 |
| | | | Found | 84.26 | 6.45 | 4.25 |

TABLE 10

| Comp. | N. M. R(δ ppm)/solv. | M. S. |
|---|---|---|
| 27 | 3.68(s, 3H), 3.72(s, 3H), 4.27(d, 1H), 4.66(d, 1H), 6.61(d, 1H), 6.76(m, 4H), 6.85(d, 2H), 6.97(d, 2H), 7.13(m, 3H), 10.21(s, 1H)/DMSO-d₆ | 358 (FAB⁻) |
| 28 | 2.23(s, 3H), 2.33(s, 3H), 4.30(d, 1H), 4.85(d, 1H), 6.71(t, 2H), 6.83~6.96(m, 5H), 7.13(m, 5H), 8.01(s, 1H)/CDCl₃ | 328 (FAB⁺) |

Preparation Example 9

Synthesis of 3-(4-methoxycarbonylphenyl-4'-methylphenyl) methylene-oxindole (Compound 30)

Suitable starting materials were used in a method similar to that of Preparation Example 1, to thereby synthesize 32.0 g (yield 82%) of 3-(4-carboxyphenyl-4'-methylphenyl) methylene-oxindole (Compound 29). The melting point and elementary analysis data are shown in Table 11, and NMR and MS spectrum data are shown in Table 12.

The resultant compound 29 (22.0 g) was added to 1000 ml methanol, and the mixture was refluxed with heat for 8 hours through use of 50 ml of conc. sulfuric acid. After completion of reaction, the reaction mixture was cooled, methanol evaporated, followed by extraction with ethyl acetate. The extract was washed with water, saturated sodium bicarbonate water, and saturated brine, and subsequently dried over sodium sulfate, and then evaporated. The resultant crude product was purified by silica gel column chromatography (chloroform), to thereby obtain 5.0 g (yield 21.9%) of the E-isomer of the title compound in the form of orange-colored crystals and 16.7 g (yield 73.2%) of the Z-isomer of the title compound in the form of yellow-colored crystals. The melting point and elementary analysis data are shown in Table 11, and NMR and MS spectrum data are shown in Table 12.

TABLE 11

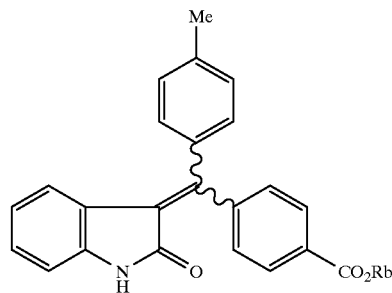

| Compound | Rb | m.p. (°C.) | | Elementary Anal. (%) | | |
|---|---|---|---|---|---|---|
| | | | | C | H | N |
| 29 (1/2H$_2$O) | H (Zisomer) | 260 (decomp.) | Calc. Found | 75.81 75.71 | 4.98 4.86 | 3.84 3.76 |
| 30-1 | Me (Zisomer) | 230~231.5 | Calc. Found | 78.03 78.20 | 5.18 5.10 | 3.79 3.79 |
| 30-2 (1/6H$_2$O) | Me (Eisomer) | 218~219 | Calc. Found | 77.40 77.46 | 5.23 5.15 | 3.76 3.67 |

TABLE 12

| Comp. | N. M. R(δ ppm)/solv. | M. S. |
|---|---|---|
| 29 | 2.42(s, 3H), 6.47(d, 1H), 6.62(t, 2H), 6.87(d, 1H), 7.11 (t, 1H), 7.14(d, 2H), 7.28(d, 2H), 7.47(d, 2H), 7.99 (d, 2H), 9.45(s, 1H)/ACETN-d$_6$ | 355 (EI$^+$) |
| 30-1 | 2.43(s, 3H), 3.91(s, 3H), 6.56(d, 1H), 6.67(t, 2H), 7.09 (t, 1H), 7.19(d, 2H), 7.23(d, 2H), 7.39(d, 2H), 8.01 (d, 2H), 8.36(brs, 1H)/CDCl$_3$ | 369 (EI$^+$) |
| 30-2 | 2.38(s, 3H), 3.96(s, 3H), 6.28(d, 1H), 6.62(t, 1H), 6.74 (d, 1H), 7.07(d, 1H), 7.16(d, 2H), 7.23(d, 2H), 7.41 (d, 2H), 8.10(d, 2H), 8.36(brs, 1H)/CDCl$_3$ | 369 (EI$^+$) |

Preparation Example 10

Synthesis of 3-(4-methoxybenzylidene)-oxindole (Compound 31)

2.0 g of oxindole was dissolved in 40 ml of ethanol, and 2.0 g of p-anisaldehyde was added thereto at room temperature. Subsequently, 1.5 ml of piperidine was added, and the mixture was refluxed with heat for 13 hours. After completion of reaction, the reaction mixture was cooled. Crystals that precipitated were collected by filtration. The resultant crude product was washed with methanol, to thereby obtain 2.6 g (yield 71%) of the title compound in the form of yellow crystals. The melting point and elementary analysis data are shown in Table 13, and NMR and MS spectrum data are shown in Table 14.

Preparation Example 11

Suitable starting materials were used in a method similar to that of Preparation Example 10, to thereby synthesize Compound 32 shown in Tables 13 and 14.

TABLE 13

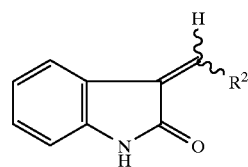

| Compound | R$^2$ | m.p. (°C.) | | Elementary Anal. (%) | | |
|---|---|---|---|---|---|---|
| | | | | C | H | N |
| 31 |  | 190 | Calc. Found | 76.48 76.68 | 5.21 5.06 | 5.57 5.61 |

TABLE 13-continued

| Compound | R² | m.p. (°C.) | | Elementary Anal. (%) | | |
|---|---|---|---|---|---|---|
| | | | | C | H | N |
| 32 | (2,6-dimethoxy-4-methyl-phenol with OMe, OH, OMe) | 208~210 | Calc. | 68.68 | 5.09 | 4.71 |
| | | | Found | 68.71 | 5.14 | 4.65 |

TABLE 14

| Comp. | N. M. R(δ ppm)/solv. | M. S. |
|---|---|---|
| 31 | 3.87, 3.88(isomers, 3H), 6.85(d, 1H), 6.95~7.07(m, 3H), 7.19(t, 1H), 7.50(d, 2H), 8.05(brs, 1H), 8.36(d, 2H)/CDCl₃ | 251 (EI⁺) |
| 32 | 3.92, 4.01(isomers, 6H), 5.89, 6.01(isomers, 1H), 6.86~7.26(m, 4H), 7.47~7.53(m, 1H), 7.77(s, 1H), 7.92(s, 1H), 8.25, 8.41 (isomers, 1H)/CDCl₃ | 297 (EI⁺) |

Preparation Example 12

Synthesis of 3-[bis(4-aminophenyl)methylene]-oxindole (Compound 33)

To 200 ml of t-amyl alcohol were poured 12.9 g of 97% oxindole, 20.0 g of 4,4'-diaminobenzophenone, and 26.43 g of potassium-t-butoxide. By use of a Molecular Sieves 4A tower which served as a dehydrator, the resultant mixture was refluxed with heat for 12 hours. Thereafter, the reaction mixture was cooled. An aqueous solution prepared by diluting 25 g of 35% HCl with 200 g water was added. The resultant mixture was stirred for 1.5 hours while being cooled with ice, and yellow crystals that precipitated were collected by filtration. The resultant crude product was washed with acetone, to thereby obtain 4.6 g (yield 15%) of the title compound in the form of yellow crystals. The melting point and elementary analysis data are shown in Table 15, and NMR and MS spectrum data are shown in Table 16.

Preparation Example 13

Suitable starting materials were used in a method similar to that of Preparation Example 12, to thereby synthesize 3-[bis(4-dimethylaminophenyl)methylene]-oxindole (Compound 34) shown in Tables 15 and 16.

TABLE 15

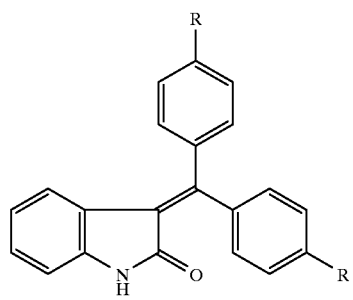

| Compound | R | m.p. (°C.) | | Elementary Anal. (%) | | |
|---|---|---|---|---|---|---|
| | | | | C | H | N |
| 33 | H₂ | >300 | Calc. | 77.04 | 5.23 | 12.83 |
| | | | Found | 75.26 | 5.13 | 12.39 |
| 34 | NMe₂ | 160 (decomp) | Calc. | 78.30 | 6.57 | 10.96 |
| | | | Found | 76.07 | 6.66 | 10.58 |

TABLE 16

| Comp. | N. M. R(δ ppm)/solv. | M. S. |
|---|---|---|
| 33 | 5.65(s, 4H), 6.39(d, 1H), 6.45(d, 2H), 6.54~6.59(m, 3H), 6.70(d, 1H), 6.88(d, 2H), 6.92~6.97(m, 3H), 7.43(d, 1H)/DMSO-d₆ | 327 (EI⁺) |
| 34 | 3.03(s, 6H), 3.06(s, 6H), 6.62~6.76(m, 7H), 7.00 (m, 1H), 7.22(d, 2H), 7.29(d, 2H), 7.65(s, 1H)/CDCl₃ | 383 (EI⁺) |

Preparation Example 14

Synthesis of 3-(di-2-pyridylmethylene)-oxindole (Compound 35)

To 50 ml of acetic acid were poured 4.2 g of 97% oxindole, 5.0 g of di-2-pyridylketone, and 20.9 g of ammonium acetate. The mixture was heated for 12 hours at 100° C. Thereafter, the solvent was evaporated, and the residue was extracted with ethyl acetate. The extract was washed with water, saturated sodium bicarbonate water, and saturated brine, and subsequently dried over sodium sulfate. The resultant crude product was purified by silica gel column chromatography (ethyl acetate), to thereby obtain 6.4 g (yield 78.8%) of the title compound in the form of yellow crystals. The melting point and elementary analysis data are shown in Table 17, and NMR and MS spectrum data are shown in Table 18.

Preparation Example 15

Suitable starting materials were used in a method similar to that of Preparation Example 14, to thereby synthesize 3-(di-2-pyridylmethylene)-5-ethoxycarbonyl-oxindole (Compound 36) shown in Tables 17 and 18.

Preparation Example 16
Synthesis of 3-(di-2-pyridylmethylene)-5-carboxyl-oxindole (Compound 37)

5.0 g of the synthesized compound, 3-(di-2-pyridylmethylene)-5-ethoxycarbonyloxindole was added to 50 ml of a 1:1 solvent mixture of methanol containing water and 2.5 g of 96% NaOH. The mixture was stirred for 6 hours at room temperature. After completion of reaction, pH of the reaction mixture was adjusted to 5 by use of 10% HCl in an ice bath, and the crystals that precipitated were collected by filtration. The crystals were washed with water, to thereby obtain 2.2 g (yield 47.5%) of the title compound in the form of orange-colored crystals. The melting point and elementary analysis data are shown in Table 17, and NMR and MS spectrum data are shown in Table 18.

TABLE 17

| Compound | R | m.p. (°C.) | | Elementary Anal. (%) | | |
|---|---|---|---|---|---|---|
| | | | | C | H | N |
| 35 | H | 207~210 | Calc. | 76.24 | 4.38 | 14.04 |
| | | | Found | 76.41 | 4.08 | 14.07 |
| 36 | CO$_2$Et | 241~243 | Calc. | 71.15 | 4.61 | 11.21 |
| | | | Found | 71.17 | 4.32 | 11.33 |
| 37 | CO$_2$H | 277~279 | Calc. | 71.15 | 4.61 | 11.21 |
| | | | Found | 71.17 | 4.32 | 11.33 |

TABLE 18

| Comp. | N. M. R(δ ppm)/solv. | M. S. |
|---|---|---|
| 35 | 6.32(d, 1H), 6.66~6.70(m, 2H), 7.12(t, 1H),7.27 (m, 1H), 7.36(m, 1H), 7.56(d, 1H), 7.64(d, 1H), 7.71~7.79(m, 2H), 8.02(s, 1H), 8.65(d, 1H), 8.74(d, 1H)/CDCl$_3$ | 299 (EI$^+$) |
| 36 | 1.28(t, 3H), 4.21(q, 2H), 6.75(d, 1H), 7.04(s, 1H), 7.29(t, 1H), 7.41(t, 1H), 7.53(d, 1H), 7.63(d, 1H), 7.75(t, 1H), 7.81~7.88(m, 2H), 8.17(s, 1H), 8.67(d, 1H), 8.79(d, 1H)/CDCl$_3$ | 371 (EI$^+$) |
| 37 | 6.83(s, 1H), 6.89(d, 1H), 7.33(t, 1H), 7.49(t, 2H), 7.67 (d, 1H), 7.77~7.81(m, 2H), 7.93(t, 1H), 8.52(d, 1H), 8.69(d, 1H), 10.94(s, 1H)/DMSO-d$_6$ | 343 (EI$^+$) |

Preparation Example 17

Suitable starting materials were used in a method similar to that of Preparation Example 10, to thereby synthesize Compounds 38–40 shown in Tables 19 and 20.

TABLE 19

| Compound | R | m.p. (°C.) | | Elementary Anal. (%) | | |
|---|---|---|---|---|---|---|
| | | | | C | H | N |
| 38 | 2-pyridyl | 209~211 | Calc. | 75.66 | 4.54 | 12.60 |
| | | | Found | 75.75 | 4.21 | 12.57 |
| 39 | 3-pyridyl | 182~184 | Calc. | 75.66 | 4.54 | 12.60 |
| | | | Found | 75.39 | 4.35 | 12.47 |
| 40 | 4-pyridyl | 228~230 | Calc. | 75.66 | 4.54 | 12.60 |
| | | | Found | 75.72 | 4.23 | 12.60 |

TABLE 20

| Comp. | N. M. R(δ ppm)/solv. | M. S. |
|---|---|---|
| 38 | 6.87(d, 1H), 6.99(t, 1H), 7.29(t, 1H), 7.48(t, 1H) 7.57 (s, 1H), 7.88(d, 1H), 7.96(t, 1H), 8.89(d, 1H), 9.00 (d, 1H), 10.63(brs, 1H)/DMSO-d$_6$ | 223 (FAB$^+$) |
| 39 | 6.86(t, 1H), 6.89(d, 1H), 7.25(t, 1H), 7.37(d, 1H), 7.56(dd, 1H), 7.63(s, 1H), 8.12(d, 1H), 8.65(d, 1H), 8.87(s, 1H), 10.67(brs, 1H)/DMSO-d$_6$ | 222 (EI$^+$) |
| E and Z | 6.86(m, 1H), 7.01(t, 1H), 7.25(t, 1H), 7.49(d, 1H), 7.72(d, 1H), 7.83(s, 1H), 8.58(d, 1H), 8.90(brs, 1H), 9.19(s, 1H), 10.67(brs, 1H)/DMSO-d$_6$ | |
| 40 | 6.84(t, 1H), 6.89(d, 1H), 7.27(t, 1H), 7.36(d, 1H), 7.56(s, 1H), 7.63(d, 2H), 8.72(d, 2H), 10.70(brs, 1H)/DMSO-d$_6$ | 222 (EI$^+$) |
| E and Z | 6.86(m, 1H), 7.01(t, 1H), 7.26(m, 1H), 7.73(d, 2H), 7.76(s, 1H), 8.11(d, 1H), 8.67(d, 2H), 10.70(brs, 1H)/DMSO-d$_6$ | |

Preparation Example 18

The compounds prepared in Preparation Examples 17 and 10 were used in a method similar to that of Preparation Example 7, to thereby synthesize Compounds 41–44 shown in Tables 21 and 22.

TABLE 21

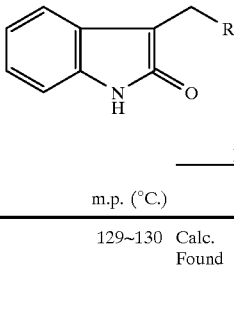

| Compound | R | m.p. (°C.) | Elementary Anal. (%) | | | |
|---|---|---|---|---|---|---|
| | | | | C | H | N |
| 41 | 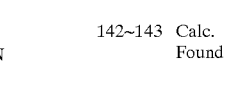 | 129~130 | Calc.<br>Found | 74.98<br>75.23 | 5.39<br>5.22 | 12.49<br>12.44 |
| 42 | 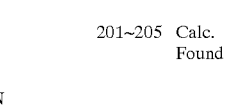 | 142~143 | Calc.<br>Found | 74.98<br>74.93 | 5.39<br>5.24 | 12.49<br>12.41 |
| 43 | 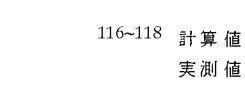 | 201~205 | Calc.<br>Found | 74.98<br>74.28 | 5.39<br>5.23 | 12.49<br>12.30 |
| 44 | (phenyl-OMe) | 116~118 | 計算値<br>実測値 | 75.87<br>75.99 | 5.97<br>5.89 | 5.53<br>5.53 |

TABLE 22

| Comp. | N. M. R(δ ppm)/solv. | M. S. |
|---|---|---|
| 41 | 3.01(dd, 1H), 3.42(dd, 1H), 3.99(d, 1H), 6.57(d, 1H), 6.76(d, 1H), 6.78(t, 1H), 7.10(t, 1H), 7.24(m, 2H), 7.70(t, 1H), 8.50(d, 1H), 10.41(brs, 1H)/DMSO-d$_6$ | 224 (EI$^+$) |
| 42 | 3.07(dd, 1H), 3.30(d, 1H), 3.85(d, 1H). 6.70(d, 1H), 6.89(t, 1H), 7.04(d, 1H), 7.11(t, 1H), 7.21(d, 1H), 7.50(d, 1H), 8.28(s, 1H), 8.34(d, 1H), 10.31(s, 1H)/DMSO-d$_6$ | 224 (EI$^+$) |
| 43 | 3.03(d, 1H), 3.30(d, 1H), 3.90(d, 1H), 6.74(d, 1H), 6.87(t, 1H), 6.98(d, 1H), 7.12(t, 1H), 7.15(d, 2H), 8.38(d, 2H), 10.36(s, 1H)/DMSO-d$_6$ | 224 (EI$^+$) |
| 44 | 2.89(d, 1H), 3.24(d, 1H), 3.65(s, 3H), 3.73(d, 1H), 6.72(d, 1H), 6.75(d, 2H), 6.84(t, 1H), 6.89(d, 1H), 7.03(d, 2H), 7.08(t, 1H), 10.27(brs, 1H)/DMSO-d$_6$ | 254 (FAB$^+$) |

Test Example 1
Pharmacological Test (Intimal Hypertrophy Inhibiting Activity in Rats)

By use of various compounds which serve as active ingredients of the present invention, the following tests (1) and (2) were performed in accordance with the method described in Journal of Clinical Investigation, 85 (1990) 2004.

(1) Test method

Groups of 14- to 15-week-old male S.D. rats were used. A 3F balloon catheter was inserted in each rat, under etherification, through the right iliac artery to the aorta. While the balloon was inflated, the endothelium of the thoracic aorta was denuded. Subsequently, the balloon catheter was removed, and an antibiotic was added dropwise into the abdominal cavity, followed by saturing. Each drug was suspended in 0.5% methylcellulose, and a dose of 10 ml/kg was orally administered once a day, starting from 2 hours after denudation. To the controls were administered 0.5% methylcellulose.

The rats were sacrificed 14 days after denudation. The thoracic aorta was removed and fixed with 10% neutrally-buffered formalin. Six segments cut out from the lower part of each sample were processed by a customary method to thereby prepare paraffin sections. Six specimens of the sections from each rat were stained with hematoxylin-eosin. The thickness of the neoplastic intima at the site of maximal hypertrophy and that of the media at the same site were measured, and the ratio of intimal thickness to media thickness was calculated. Assessment was performed in terms of percentage of intimal hypertrophy inhibition as determined from the intima/media thickness ratios, using as standards the data from the groups to which drugs had not been administered. The results are shown in Table 23.

The following four different compounds (a)–(d) were used as comparative compounds:

(a): disclosed in Japanese Patent Application Laid-Open (kokai) No. 6-135829 (Tranilast);

(b): disclosed in Japanese Patent Application Laid-Open (kokai) No. 62-29570;

(c): disclosed in Japanese Patent Publication (kokoku) No. 7-108900; and (d): disclosed in Japanese Patent Application Laid-Open (kokai) No. 6-501494.

(a) 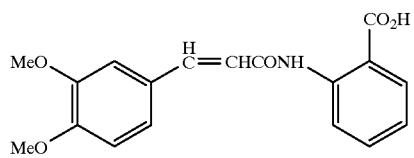

(b) 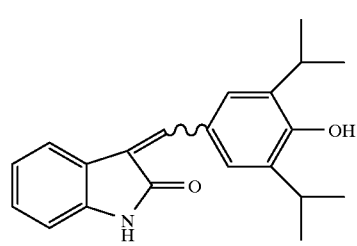

(c) 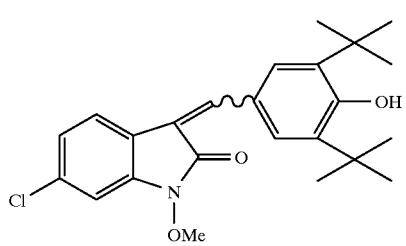

(d) 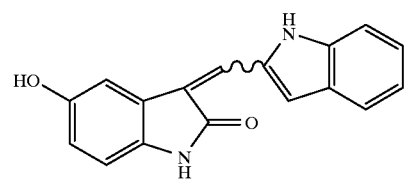

TABLE 23

| Compound | Dose (mg/kg) | Inhibition (%) |
|---|---|---|
| 1 | 30 | 33.2 |
| (Crystal 1) | 100 | 46.6 |
| 2 | 30 | 36.5 |
|  | 100 | 42.3 |
| 5 | 30 | 14.8 |
| 6 | 30 | 14.7 |
| 7 | 30 | 34.2 |
| 8 | 30 | 28.9 |
| 9 | 30 | 26.6 |
| 10 | 30 | 14.8 |
| 13 | 30 | 10.9 |
| 16 | 30 | 21.1 |
| 17 | 30 | 20.9 |
| 18 | 30 | 34.8 |
| 20 | 30 | 7.2 |
| 22 | 30 | 28.0 |
| 24 | 30 | 35.1 |
| 25 | 30 | 7.6 |
| 27 | 30 | 19.7 |
| 28 | 30 | 28.4 |
| 31 | 30 | 40.0 |
| 32 | 30 | 34.0 |
| a | 30 | 7.1 |
|  | 100 | 18.1 |
| b | 30 | −26.0 |
| c | 30 | −8.6 |
| d | 30 | −0.1 |

(2) Test method

Groups of 13- to 14-week-old male S.D. rats were used. A 2F balloon catheter was inserted in each rat under etherification through the right iliac artery to the left carotid artery. While the balloon was inflated, the endothelium of the left caroid artery was denuded. Subsequently, the balloon catheter was removed, and an antibiotic was added dropwise into the abdominal cavity, followed by saturing. Each drug was suspended in 0.5% methylcellulose, and a dose of 10 ml/kg was orally administered once a day, starting from 2 hours after denudation. To the controls were administered 0.5% methylcellulose.

The rats were sacrificed 14 days after denudation The left carotid artery was removed and fixed, through perfusion, with 10% buffered formalin. Each sample was divided into six segments and the segments were processed by a customary method to thereby prepare paraffin sections. Six specimens of the sections from each rat were stained with hematoxylin-eosin. The area of the neoplastic intima and that of the media were measured, and assessment was performed in terms of percentage of intimal hypertrophy inhibition as determined from the intima/media area ratios, using as standards the data from the groups to which drugs had not been administered. The results are shown in Table 24.

TABLE 24

| Compound | Dose (mg/kg) | Inhibition (%) |
|---|---|---|
| 33 | 30 | 32.7 |
| 35 | 30 | 36.8 |
| 38 | 30 | 42.0 |

From the above-described test results, it is clear that the compound of formula (1), i.e., the active ingredient of the present invention, provided effect equal to or higher than that of tranilast (Comparative Example (a)) which is on the way toward clinical development, showing remarkably excellent intimal hypertrophy inhibiting activity as compared with comparative compounds (b) through (d), which are analogs of the compound of the present invention. Therefore, the compound of formula (1) is useful as an intimal hypertrophy inhibitor.

Example 1 Tablets

| | |
|---|---|
| Compound 1 (Crystal 1) | 200 mg |
| Cornstarch | 50 mg |
| Microcrystalline cellulose | 50 mg |
| Hydroxypropylcellouse | 15 mg |
| Lactose | 47 mg |
| Talc | 2 mg |
| Magnesium stearate | 2 mg |
| Ethylcellulose | 30 mg |
| Stearic monoglyceride | 4 mg |

The above formulation was processed with a routine method, to thereby prepare tablets each weighing 400 mg.

Example 2 Granules

| | |
|---|---|
| Compound 2 | 300 mg |
| Lactose | 540 mg |
| Cornstarch | 100 mg |
| Hydroxypropylcellulose | 50 mg |
| Talc | 10 mg |

The above formulation was processed with a routine method, to thereby prepare packages of granules each package weighing 1,000 mg.

Example 3 Capsules

| | |
|---|---:|
| Compound 7 | 200 mg |
| Lactose | 30 mg |
| Cornstarch | 50 mg |
| Microcrystalline cellulose | 10 mg |
| Magnesium stearate | 3 mg |

The above formulation was processed with a routine method, to thereby prepare capsules each weighing 293 mg.

Example 4 Injection Liquid

| | |
|---|---:|
| Compound 23 | 100 mg |
| Sodium chloride | 3.5 mg |
| Distilled water for injection | Suitable amount |
| | (2 mg per ampule) |

The above formulation was processed with a routine method, to thereby prepare an injection liquid.

Example 5 Syrup

| | |
|---|---:|
| Compound 29 | 200 mg |
| Purified sucrose | 60 g |
| Ethyl p-hydroxybenzoate sucrose | 5 mg |
| Propyl p-hydroxybenzoate sucrose | 5 mg |
| Perfume | Suitable amount |
| Colorant | Suitable amount |
| Purified water | Suitable amount |

The above formulation was processed with a routine method, to thereby prepare a syrup.

Example 6 Suppositories

| | |
|---|---:|
| Compound 33 | 300 mg |
| Witepsole W-35 | 1,400 mg |
| (Registered trademark of Dynamite-Nobel; | |
| Mixture of mono-, di-, and tri- glycerides | |
| of saturated fatty acid ranging from | |
| lauric acid to stearic acid) | |

The above formulation was processed with a routine method, to thereby prepare suppositories.

Industrial Applicability

The intimal hypertrophy inhibitor of the present invention which contains as the active ingredient an oxindole derivative or a salt thereof exhibits excellent inhibitory action against intimal hypertrophy, and thus is useful as a preventive/therapeutic/ameliorating agent for proliferative vascular diseases such as restenosis after PTCA (percutaneous transluminal coronary angioplasty), arteriosclerosis, peripheral embolism, and angiitis.

We claim:

1. A preventive and therapeutic method for treating intimal hypertrophy, characterized by administering to a patient, in need thereof, a therapeutically effective amount of an oxindole derivative compound represented by the following formula (I) or a salt thereof:

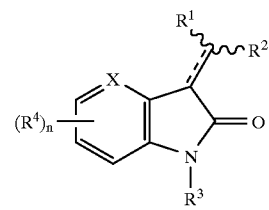

(wherein $R^1$ represents a hydrogen atom; a phenyl group which may be substituted by a lower alkyl group, a lower alkoxy group, a lower alkylaminoalkoxy group, a hydroxy group, an amino group, a lower alkylamino group, or a halogen atom; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group; wherein (a) in the case where $R^1$ is a hydrogen atom:
$R^2$ represents a phenyl group which may be substituted by a hydroxy group or a lower alkoxy group; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group; each of $R^3$ and $R^4$ represents a hydrogen atom; x represents CH; and the broken/solid double line denotes a double bond; n represents the number 3;

(b) in the case where $R^1$ is a phenyl group which may be substituted by a lower alkyl group, a lower alkoxy group, a lower alkylaminoalkoxy group, a hydroxy group, an amino group, a lower alkylamino group, or a halogen atom; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group:
$R^2$ represents a phenyl group which may be substituted by a lower alkyl group, a lower alkoxy group, a lower alkylaminoalkoxy group, a lower alkoxycarbonyl group, a carboxyl group, a hydroxy group, an amino group, a lower alkylamino group, or a halogen atom; or a pyridyl group which may be substituted by a lower alkyl group, a lower alkoxy group, a lower alkylaminoalkoxy group, a hydroxy group, an amino group, a lower alkylamino group, a halogen atom, a lower alkoxycarbonyl group, or a carboxyl group; $R^3$ represents a hydrogen atom; a lower alkyl group which may be substituted, a benzyl group which may be substituted, benzenesulfonyl group which may be substituted, or acyl group; $R^4$ represents a hydrogen atom, a lower alkoxy group, a halogen atom, an amino group, a carboxyl group, a lower alkylamino group, a lower alkoxycarbonyl group, a phenylcarbamoyl group which may be substituted, or a trifluoromethyl group; x represents CH or N; n represents a number between 0 and 4 inclusive that indicates the number of substituents, and the broken/solid double line denotes a single bond or a double bond).

2. The method according to claim 1, wherein, in formula (1), $R^1$ represents a hydrogen atom, $R^2$ represents a phenyl group which may be substituted by a hydroxy group or a lower alkoxyl group; or a pyridyl group which may be substituted by a lower alkoxy group; each of $R^3$ and $R^4$ represents a hydrogen atom; X represents CH; and the broken/solid double line represents a double bond.

3. The method according to claim 2, wherein, in formula (1), $R^2$ represents a pyridyl group, 4-methoxyphenyl group, or 3,5-dimethoxy-4-hydroxyphenyl group.

4. The method according to claim 1, wherein, in formula (1), $R^1$ and $R^2$ may be identical to or different from each other, and each of $R^1$ and $R^2$ represents a phenyl group which may be substituted by a lower alkyl group, a lower alkoxy group, a lower alkylaminoalkoxy group, a hydroxy group, an amino group, a lower alkylamino group, or a halogen atom; or a pyridyl group which may be substituted by a lower alkoxy group; $R^3$ represents a hydrogen atom; a lower alkyl group which may be substituted by a lower alkoxycarbonyl group, a lower alkylamino group, or a lower alkylcarbamoyl group; a benzyl group which may be substituted, on the phenyl ring, by a lower alkoxy group or a lower alkoxycarbonyl group; a benzoyl group which may be substituted, on the phenyl ring, by a lower alkoxycarbonyl group; or a benzenesulfonyl group which may be substituted, on the phenyl ring, by a lower alkyl group; and $R^4$ represents a hydrogen atom, an amino group, a carboxyl group, a lower alkylamino group, or a lower alkoxycarbonyl group.

5. The method according to claim 4, wherein, in formula (1), $R^1$ and $R^2$ may be identical to or different from each other, and each of $R^1$ and $R^2$ represents a pyridyl group; or a phenyl group which may be substituted by methyl, ethyl, butyl, methoxy, amino, dimethylamino, dimethylaminoethoxy, hydroxy, or chlorine; $R^3$ represents a hydrogen atom; a lower alkyl group which may be substituted by methoxycarbonyl, ethoxycarbonyl, dimethylamino, or dimethylcarbamoyl; a benzyl group which may be substituted, on the phenyl ring, by a methoxycarbonyl group; or a benzenesulfonyl group which may be substituted, on the phenyl ring, by a methyl group; and $R^4$ represents a hydrogen atom, an amino group, a carboxyl group, a di- lower alkylamino group, or a lower alkoxycarbonyl group; X represents CH; and the broken/solid double line represents a double bond.

6. The method according to claim 5, wherein, in formula (1), $R^1$ and $R^2$ may be identical to or different from each other, and each represents a pyridyl group, a phenyl group, a tolyl group, a butylphenyl group, a methoxyphenyl group, a hydroxyphenyl group, or a dimethylaminoethoxyphenyl group; $R^3$ represents a hydrogen atom, a methyl group, a methoxycarbonylpentyl group, an ethoxycarbonylmethyl group, a dimethylaminoethyl group, a dimethylcarbamoylmethyl group, a methoxycarbonylbenzyl group, or a toluenesulfonyl group; $R^4$ is a hydrogen atom, an amino group, a carboxyl group, a dimethylamino group, or an ethoxycarbonyl group; X represents CH; n represents 1 or 2; and the broken/solid double line represents a double bond.

* * * * *